(12) United States Patent
Dziura et al.

(10) Patent No.: US 8,860,937 B1
(45) Date of Patent: Oct. 14, 2014

(54) METROLOGY SYSTEMS AND METHODS FOR HIGH ASPECT RATIO AND LARGE LATERAL DIMENSION STRUCTURES

(71) Applicant: KLA-Tencor Corporation, Milpitas, CA (US)

(72) Inventors: Thaddeus Gerard Dziura, San Jose, CA (US); Xuefeng Liu, San Jose, CA (US); David Y. Wang, Santa Clara, CA (US); Jonathan Madsen, Los Altos, CA (US); Alexander Kuznetsov, Mountain View, CA (US); Johannes D. de Veer, Menlo Park, CA (US); Shankar Krishnan, Santa Clara, CA (US); Derrick Shaughnessy, San Jose, CA (US); Andrei Shchegrov, Campbell, CA (US)

(73) Assignee: KLA-Tencor Corp., Milpitas, CA (US)

( * ) Notice: Subject to any disclaimer, the term of this patent is extended or adjusted under 35 U.S.C. 154(b) by 11 days.

(21) Appl. No.: 13/743,304

(22) Filed: Jan. 16, 2013

Related U.S. Application Data

(60) Provisional application No. 61/718,184, filed on Oct. 24, 2012.

(51) Int. Cl.
  *G01N 21/00*  (2006.01)
  *G01N 21/47*  (2006.01)

(52) U.S. Cl.
  CPC ..................................... *G01N 21/47* (2013.01)
  USPC ......... 356/237.4; 356/625; 356/369; 356/601

(58) Field of Classification Search
  CPC ............ G01N 21/9501; G01N 21/956; G01N 21/211; G01N 2021/213; G01N 21/88; G01B 11/0625; G01B 11/0641; G01B 11/24; G01B 2210/56; G03F 7/7065
  USPC ................... 356/237.1–237.5, 369, 601–613, 356/625–632
  See application file for complete search history.

(56) References Cited

U.S. PATENT DOCUMENTS

| | | | |
|---|---|---|---|
| 5,072,128 A | 12/1991 | Hayano et al. | |
| 5,264,912 A | 11/1993 | Vaught et al. | |

(Continued)

FOREIGN PATENT DOCUMENTS

| | | |
|---|---|---|
| EP | 1 333 328 | 8/2003 |
| WO | 2012/082501 | 6/2012 |

OTHER PUBLICATIONS

Arceo et al., "Semiconductor metrology beyond 22nm: 3D memory metrology," Solid State Technology (online edition), Feb. 16, 2012.

(Continued)

*Primary Examiner* — Hoa Pham
(74) *Attorney, Agent, or Firm* — Ann Marie Mewherter

(57) ABSTRACT

Various metrology systems and methods for high aspect ratio and large lateral dimension structures are provided. One method includes directing light to one or more structures formed on a wafer. The light includes ultraviolet light, visible light, and infrared light. The one or more structures include at least one high aspect ratio structure or at least one large lateral dimension structure. The method also includes generating output responsive to light from the one or more structures due to the light directed to the one or more structures. In addition, the method includes determining one or more characteristics of the one or more structures using the output.

19 Claims, 5 Drawing Sheets

(56) References Cited

U.S. PATENT DOCUMENTS

| | | | |
|---|---|---|---|
| 5,386,119 | A | 1/1995 | Ledger |
| 5,608,526 | A | 3/1997 | Piwonka-Corle et al. |
| 5,684,565 | A | 11/1997 | Oshida et al. |
| 5,859,424 | A | 1/1999 | Norton et al. |
| 6,483,580 | B1 | 11/2002 | Xu et al. |
| 6,788,404 | B2 | 9/2004 | Lange |
| 6,891,627 | B1* | 5/2005 | Levy et al. ............... 356/625 |
| 6,900,892 | B2 | 5/2005 | Shchegrov et al. |
| 7,126,699 | B1* | 10/2006 | Wihl et al. ............... 356/625 |
| 7,358,494 | B1 | 4/2008 | Gao et al. |
| 7,478,019 | B2 | 1/2009 | Zangooie et al. |
| 8,073,240 | B2 | 12/2011 | Fischer et al. |
| 8,237,213 | B2 | 8/2012 | Liu |
| 2002/0001364 | A1 | 1/2002 | Opsal et al. |
| 2002/0006044 | A1 | 1/2002 | Harbers et al. |
| 2002/0060791 | A1 | 5/2002 | Stumbo et al. |
| 2002/0109110 | A1 | 8/2002 | Some et al. |
| 2003/0020009 | A1 | 1/2003 | Sugiyama et al. |
| 2004/0179738 | A1 | 9/2004 | Dai et al. |
| 2004/0207836 | A1 | 10/2004 | Chhibber et al. |
| 2004/0222358 | A1 | 11/2004 | Bui et al. |
| 2004/0235205 | A1 | 11/2004 | Levy et al. |
| 2005/0133693 | A1 | 6/2005 | Fouquet et al. |
| 2005/0269522 | A1 | 12/2005 | Farmer et al. |
| 2006/0164649 | A1 | 7/2006 | Rosengaus |
| 2006/0281266 | A1* | 12/2006 | Wells ............... 438/299 |
| 2007/0012887 | A1 | 1/2007 | Letz et al. |
| 2007/0020784 | A1 | 1/2007 | Timans et al. |
| 2007/0195332 | A1* | 8/2007 | Hwang et al. ............... 356/511 |
| 2008/0277749 | A1 | 11/2008 | Enichlmair et al. |
| 2009/0014624 | A1 | 1/2009 | Blees et al. |
| 2010/0008588 | A1 | 1/2010 | Feldkhun et al. |
| 2011/0170090 | A1 | 7/2011 | Naftali et al. |
| 2011/0278441 | A1 | 11/2011 | Vermeulen et al. |
| 2011/0320149 | A1 | 12/2011 | Lee et al. |
| 2012/0171835 | A1 | 7/2012 | Liu et al. |
| 2012/0257213 | A1* | 10/2012 | Schonleber ............... 356/485 |
| 2013/0116978 | A1 | 5/2013 | Yoo et al. |

OTHER PUBLICATIONS

Gostein et al., "Measuring deep-trench structures with model-based IR," Solid State Technology, vol. 49, No. 3, 38-42 (2006).

International Search Report and Written Opinion for PCT/US2013/066677 mailed Jan. 20, 2014.

Jang et al., "Vertical Cell Array using TCAT (Terabit Cell Array Transistor) Technology for Ultra High Density NAND Flash Memory," 2009 Symposium on VLSI Technology Digest of Technical Papers, pp. 192-193, paper 10A-4, 2009.

Nahory et al., "Band gap versus composition and demonstration of Vegard's law for In1-xGaxAsyP1-y lattice matched to InP," Appl. Phys. Lett., 33(7), pp. 659-661, Oct. 1, 1978.

Scheel et al., "Electronic band structure of high-index silicon nanowires," phys. stat. sol. (b), pp. 1-6, Aug. 22, 2005.

\* cited by examiner

METROLOGY SYSTEMS AND METHODS FOR HIGH ASPECT RATIO AND LARGE LATERAL DIMENSION STRUCTURES

BACKGROUND OF THE INVENTION

1. Field of the Invention

The present invention generally relates to metrology systems and methods for high aspect ratio and large lateral dimension structures.

2. Description of the Related Art

The following description and examples are not admitted to be prior art by virtue of their inclusion in this section.

As stated in "Semiconductor metrology beyond 22 nm: 3D memory metrology," Arceo et al., Solid State Technology (online edition), Feb. 16, 2012, which is incorporated by reference as if fully set forth herein, summarizing state-of-the-art metrology choices for high aspect ratio (HAR) structures, "Many optical techniques, especially those that operate off-axis near the critical angle, suffer from a very small fraction of the interrogating light reaching the feature bottom, and reflect upwards to the detector. Thus, in most cases, the various metrology techniques in their present forms will suffer low signal-to-noise ratios (SNRs) on such features." In fact, no fast throughput and reliable metrology exists for measuring HAR structures, which will continue to be problematic as aspect ratios increase to 30:1, 100:1 and beyond. While techniques such as critical dimension (CD) small angle X-ray scatterometry (CD-SAXS), normal incidence reflectometry, and scatterometry are being explored and are also mentioned in the above reference, no adequate solution has been found yet. Meanwhile, the ability to measure CDs, defining the shapes of holes and trenches, is critical in achieving desired yields and high performance levels of devices.

Other challenges that exist in semiconductor device metrology are related to targets that have large lateral scales, e.g., on the order of 1 micron or larger. Since optical CD metrologies are predominantly designed for periodic targets, relatively large pitch targets can generate multiple diffraction orders that can contaminate zeroth order diffraction measurements. Applications of this type include SRAM, in-cell flash, and others.

Existing and proposed methods include the following: top view CD scanning electron microscopy (CD-SEM) that lacks the ability to provide details of 3D structures; cross-sectional SEM (X-SEM) that is destructive and cannot be used for inline metrology; CD-SAXS that has not yet been demonstrated to achieve high throughput capabilities required by the semiconductor industry; optical scatterometry CD metrology that is high throughput but is limited by SNR due to the limited light penetration into HAR structures; model-based infrared reflectometry (MBIR) (see, e.g., "Measuring deep-trench structures with model-based IR," by Gostein et al., Solid State Technology, vol. 49, no. 3, Mar. 1, 2006, which is incorporated by reference as if fully set forth herein) that has been used for metrology of HAR DRAM structures but lacks the resolution provided by shorter wavelengths and has measurement spot sizes that are too large for semiconductor metrology; and atomic force microscopy (AFM) that cannot measure substantially high aspect ratio structures and has relatively low throughput. In summary, optical CD metrology is desirable but currently lacks the ability to measure the detailed profile of structures with micron scale depths and lateral dimensions in a relatively small spot (e.g., less than 50 microns, or even more preferably, less than 30 microns).

Accordingly, it would be advantageous to develop methods and systems for determining characteristics of structures formed on a wafer that do not have one or more of the disadvantages described above.

SUMMARY OF THE INVENTION

The following description of various embodiments is not to be construed in any way as limiting the subject matter of the appended claims.

One embodiment relates to a system configured to determine one or more characteristics of one or more structures formed on a wafer. The system includes an illumination subsystem configured to direct light to the one or more structures formed on the wafer. The light includes ultraviolet (UV) light, visible light, and infrared (IR) light. The one or more structures include at least one high aspect ratio (HAR) structure or at least one large lateral dimension structure. The system also includes a detection subsystem configured to generate output responsive to light from the one or more structures due to the light directed to the one or more structures. In addition, the system includes a computer subsystem configured to determine one or more characteristics of the one or more structures using the output. The system may be further configured as described herein.

Another embodiment relates to a method for determining one or more characteristics of one or more structures formed on a wafer. The method includes directing light to the one or more structures formed on the wafer. The light includes UV light, visible light, and IR light. The one or more structures include at least one HAR structure or at least one large lateral dimension structure. The method also includes generating output responsive to light from the one or more structures due to the light directed to the one or more structures. In addition, the method includes determining one or more characteristics of the one or more structures using the output.

Each of the steps of the method described above may be further performed as described herein. In addition, the method described above may include any other step(s) of any other method(s) described herein. Furthermore, the method described above may be performed by any of the systems described herein.

BRIEF DESCRIPTION OF THE DRAWINGS

Further advantages of the present invention will become apparent to those skilled in the art with the benefit of the following detailed description of the preferred embodiments and upon reference to the accompanying drawings in which.

Figure 1:
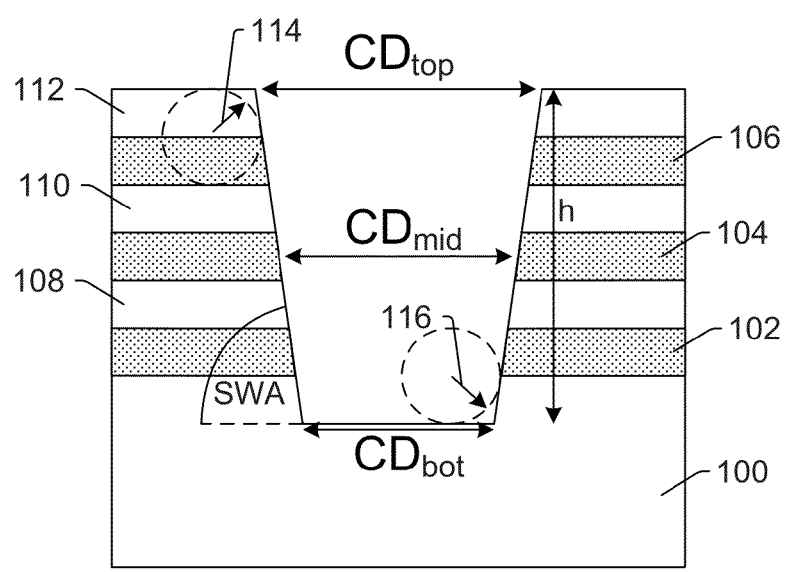
FIG. 1 is a schematic diagram illustrating a cross-sectional view of one example of one or more structures for which one or more characteristics may be determined by the embodiments described herein.

While the invention is susceptible to various modifications and alternative forms, specific embodiments thereof are shown by way of example in the drawings and are herein described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

The embodiments described herein generally relate to methods and systems for metrology of semiconductor devices with high aspect ratio (HAR) and/or large lateral dimension structures. The embodiments enable optical critical dimension (CD), film, and composition metrology for semiconductor devices with HAR (such as VNAND, TCAT, etc.) and, more generally, for complex devices that are challenging for optical metrology due to relatively low light penetration into the structure(s) being measured.

As used herein, the term "HAR structure" refers to any structure characterized by an aspect ratio that exceeds 10:1 and may be as high as 100:1 in future generation devices. HAR structures often include hard mask layers (see, for example, U.S. Pat. No. 8,237,213 to Liu issued on Aug. 7, 2012, which is incorporated by reference as if fully set forth herein) to facilitate etch processes for HARs. In addition to vertical NAND or TCAT structures, the embodiments described herein can be used for other HAR structures where light penetration into the bottom layer(s) of the structures is a metrology-limiting factor. For example, DRAM includes some such structures where the depth of deep trenches or holes etched into the substrate must be measured.

The embodiments also provide a method for metrology of targets with large lateral dimension structures. As used herein, the term "large lateral dimension structure" refers to any structure whose largest lateral dimension is on the order of 0.5 micron or larger. "Lateral dimension" is generally defined as the dimension of a structure in a direction substantially parallel to an upper surface of the wafer on which the structure is formed.

FIG. 1 illustrates one example of a structure for which one or more characteristics can be determined by the embodiments described herein. In particular, FIG. 1 shows a HAR structure. In one embodiment, the at least one HAR structure includes alternating layers of different materials having different optical properties. For example, as shown in FIG. 1, the structure may include oxide layer 100 on which alternating layers of silicon (e.g., silicon layers 102, 104, and 106) and oxide (e.g., oxide layers 108, 110, and 112) have been formed. An opening has been formed through the layers and into the bottommost oxide layer 100 to form a trench in the wafer (not shown in FIG. 1). As can be seen in FIG. 1, the width of the trench may vary from the top of the trench to the bottom of the trench. Some of the one or more characteristics that may be determined by the embodiments described herein for such a structure are shown in FIG. 1 and include height, h, CD at the top of the trench, $CD_{top}$, CD at the middle of the trench, $CD_{mid}$, CD at the bottom of the trench, $CD_{bot}$, side angle (SWA), radius 114 at the top of the trench, $r_{top}$, and radius 116 at the bottom of the trench, $r_{foot}$.

FIG. 1 is meant to illustrate just one general example of a structure that can be measured by the embodiments described herein. In general, the embodiments described herein can be used to measure one or more characteristics of any HAR or large lateral dimension structure such as the TCAT memory structures that are illustrated by J. Jang et al., in "Vertical cell array using TCAT (Terabit Cell Array Transistor) technology for ultra high density NAND flash memory," 2009 Symposium on VLSI Technology Digest on Technical Papers, pp. 192-193, paper 10A-4, which is incorporated by reference as if fully set forth herein.

Figure 2:
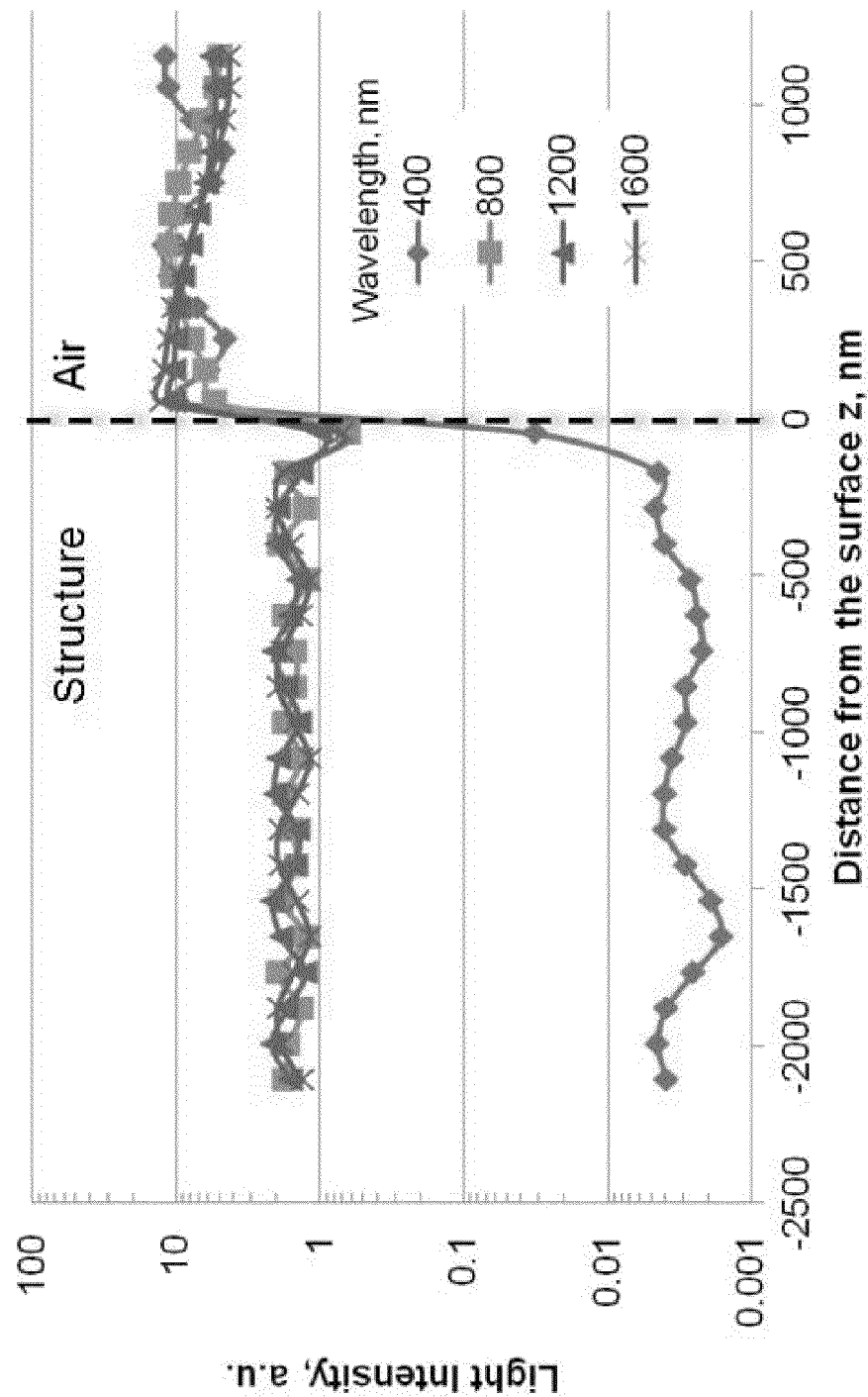
FIG. 2 is a plot illustrating the intensity of different wavelengths of light as a function of distance from the surface of one or more structures that may be measured by the embodiments described herein.

A challenge for metrology is illustrated in FIG. 2, which shows electromagnetic field intensity calculations performed by the inventors. When using shorter wavelengths in the ultraviolet (UV) and visible ranges (e.g., wavelengths less than 600 nm), the penetration of light into a structure can be strongly attenuated. This attenuation generally holds for both ellipsometer (oblique incidence) and reflectometer (near-normal or normal incidence) configurations. One reason for this can be hard mask layer(s), which can be made of polysilicon that is not transparent at shorter wavelengths. Another factor that can affect the light penetration is the multiple alternating layer design of some memory devices. Typical physical thicknesses of such alternating layer pairs can be in the range of 20 nm to 50 nm, and optical thicknesses (physical thickness multiplied by refractive index) can be in the range of 30 nm to 100 nm at near normal incidence and thicker at oblique incidence.

As is known in optical coating design, multiple layer stacks of two materials with different indices of refraction can produce relatively high reflection dielectric mirror coatings with spectrally and angularly wide stopbands. Such a design is especially efficient at wavelengths and thicknesses corresponding to the quarter wavelength condition, which ensures maximum reflection due to optical interference phenomena. Such coating stacks are also known as distributed Bragg reflectors. However, even when film thicknesses are not exactly quarter wavelength, effective reflection can be achieved. This reflection contributes to relatively low penetration of photons into the structure. As a solution proposed herein, wavelengths (and/or angles) outside of the stopband should be used.

The measurement of deep structures below an opaque hard mask or other non-transparent or partially transparent layers can also be greatly enhanced by the use of longer wavelengths. Specifically, in the case of HAR memory structures, the optimum metrology recipe corresponds to extending the wavelength range into the infrared (IR) spectral region.

The inventors realized that combining IR and visible wavelength capability in a single system is critical for measuring the details of complex 3D structures. Broadly speaking, relatively long wavelengths should be used to penetrate deep into a structure (or to provide suppression of high diffraction orders for structures with relatively large pitch). The use of relatively short wavelength(s) may still be critical to provide dimensional information about structures accessible to relatively short wavelengths (normally, top level layers) as well as relatively small CD and roughness features. In some cases, the use of longer wavelengths can be beneficial for measuring dimensional characteristics of targets with relatively rough surfaces or interfaces, due to the generally lower sensitivity of longer wavelengths to roughness.

While increasing wavelength ranges from a typical range of 190 nm to 900 nm (or even 150 nm to 900 nm) to a broader wavelength range (e.g., 190 nm to 2000 nm or even 150 nm to 2000 nm) poses several design problems for semiconductor optical metrology tools, these problems have been resolved as described herein and could not be addressed properly in previous IR optics metrology devices.

Figure 3:
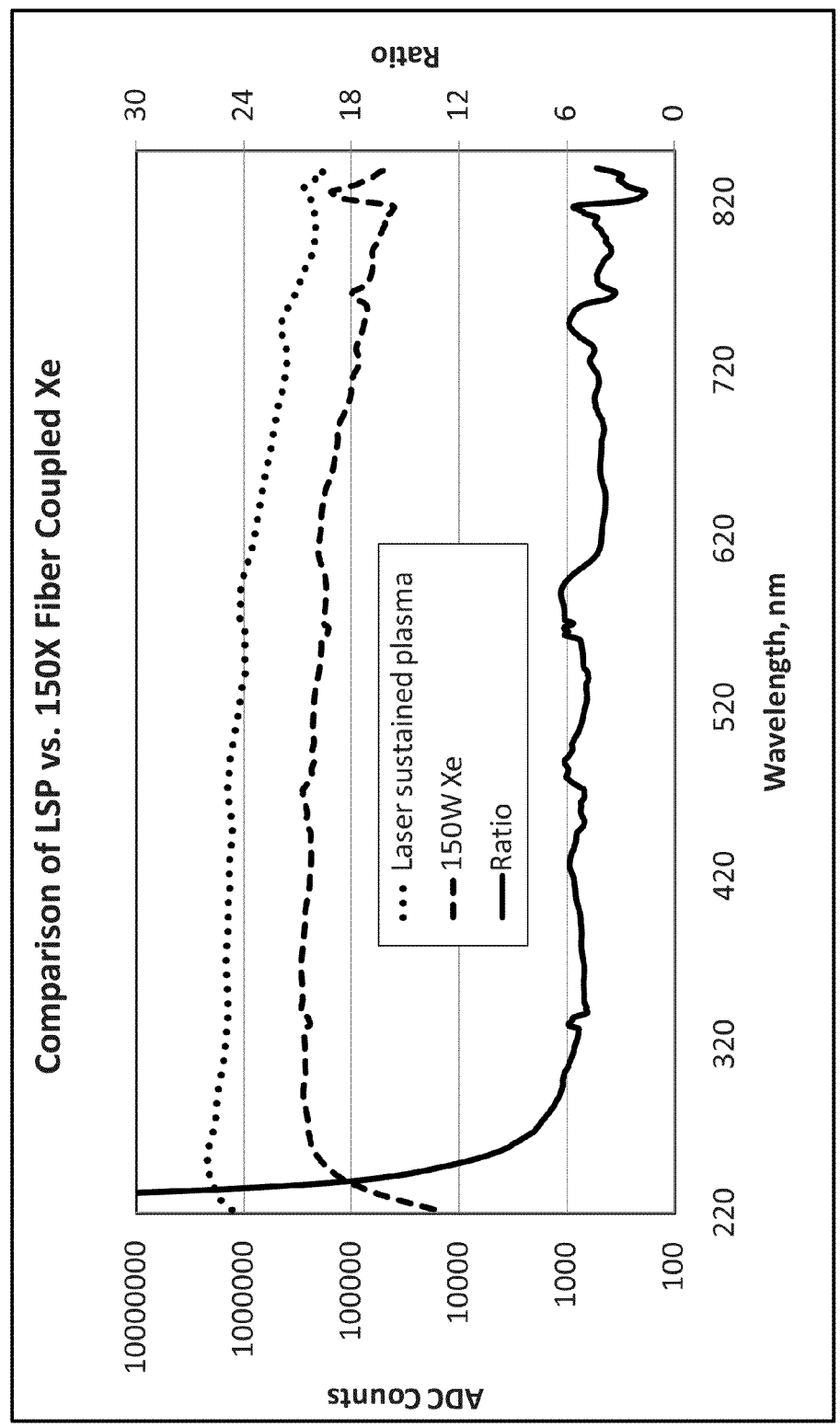
FIG. 3 is a plot illustrating the analog-to-digital converter (ADC) counts versus wavelength for different light sources.

One obstacle in IR+visible+UV system design is a shortage of light, which is limited by a viable source producing enough photons across the desired range of wavelengths. However, a laser-driven plasma source can overcome the shortage of photons. For example, a comparison of photons generated by a 12000 KCT laser-sustained plasma light source (LSP) and a 75 W, 6000 KCT Xe lamp, via Blackbody calculations (assuming full opacity), showed that the LSP produced significantly more photons than the Xe lamp across the entire wavelength range from 150 nm to 2000 nm. In addition, as can be seen in FIG. 3, the analog to digital converter (ADC) counts as a function of wavelength from an LSP are significantly higher than a 150 W fiber-coupled Xe lamp across an entire wavelength range from 220 nm to 820 nm. An LSP is also more than 10× brighter than a Xe lamp in the UV and deep UV (DUV). Furthermore, an LSP is also 5× to 8× brighter than a Xe lamp in the IR. Therefore, an LSP can be used to achieve the light levels required for the metrology described herein that cannot be achieved with a traditional light source.

Figure 4:
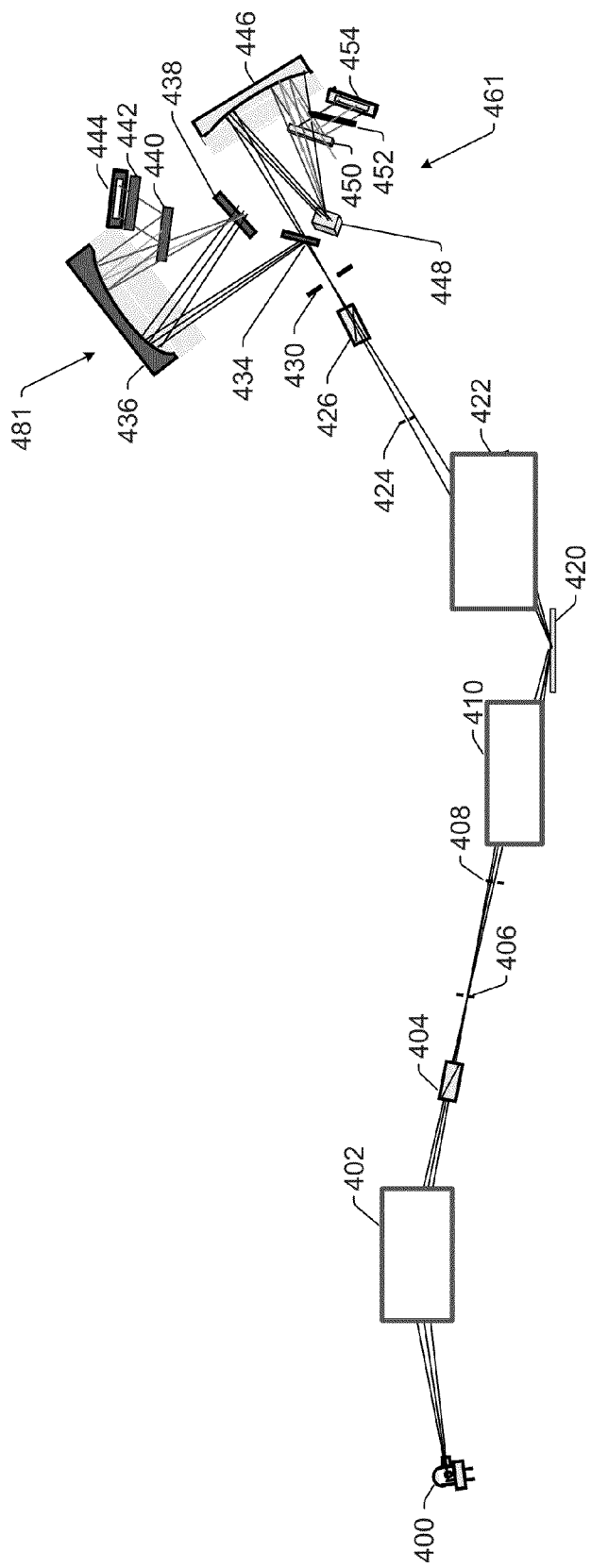
FIG. 4 is a schematic diagram illustrating a side view of one embodiment of a system configured to determine one or more characteristics of one or more structures formed on a wafer.

FIG. 4 illustrates one embodiment of a system configured to determine one or more characteristics of one or more structures formed on a wafer. The system includes an illumination subsystem configured to direct light to the one or more structures formed on the wafer. The light includes UV light, visible light, and IR light. The one or more structures may be configured as described herein. For example, the one or more structures include at least one HAR structure or at least one large lateral dimension structure.

In the embodiment shown in FIG. 4, the illumination subsystem is shown to include light source 400, one or more optical filters 402, polarizing component 404, field stop 406, aperture stop 408, and one or more optical elements 410 with reflective power. In one embodiment, the illumination subsystem includes at least one LSP. For example, light source 400 may be an LSP. One or more optical filters 402 may be used to control light level and/or spectral output of the illumination subsystem. Optical filter(s) 402 may include a multi-zone filter configured as described further herein. Polarizing component 404 may be used to generate the desired polarization state exiting the illumination subsystem. The polarizing component can be a polarizer and/or a compensator. The polarizing component can be fixed, rotatable or rotating and may include any suitable commercially available polarizing component. Although the illumination subsystem is shown in FIG. 4 to include one polarizing component, the illumination subsystem may include more than one polarizing component. Field stop 406 controls the field of view (FOV) of the illumination subsystem and may include any suitable commercially available field stop. Aperture stop 408 controls the numerical aperture (NA) of the illumination subsystem and may include any suitable commercially available aperture stop. Light from light source 400 is directed through one or more optical elements 410 with reflective power to be focused on one or more structures (not shown in FIG. 4) on wafer 420. The illumination subsystem may include any type and arrangement of optical filter(s) 402, polarizing component 404, field stop 406, aperture stop 408, and optical element(s) 410 known in the art of spectroscopic ellipsometry, reflectometry and scatterometry.

The system also includes a detection subsystem configured to generate output responsive to light from the one or more structures due to the light directed to the one or more structures. In the embodiment shown in FIG. 4, the detection subsystem is shown to include one or more optical elements 422 with reflective power, aperture stop 424, polarizing component 426, and field stop 430. One or more optical elements 422 may include any suitable such elements and may collect light from the one or more structures formed on wafer 420. Aperture stop 424 controls the NA of the detection subsystem.

Polarizing component 426 may be used to analyze the desired polarization state. The polarizing component can be a polarizer or a compensator. The polarizing component can be fixed, rotatable or rotating and may include any suitable commercially available polarizing component. In addition, although the detection subsystem is shown to include one polarizing component, the detection subsystem may include more than one polarizing component.

Field stop 430 controls the FOV of the detection subsystem. The detection subsystem takes light reflected off wafer 420 and directs the light through one or more optical elements 422 with reflective power and polarizing component 426 to be focused on field stop 430, which may be used as a spectrometer slit for spectrometer subsystems 461 and 481 of the detection subsystem. However, field stop 430 may be located at or near a spectrometer slit of spectrometer subsystems 461 and 481.

The detection subsystem may include any type and arrangement of optical element(s) 422, aperture stop 424, polarizing component 426, and field stop 430 known in the art of spectroscopic ellipsometry, reflectometry and scatterometry. In the embodiment shown in FIG. 4, optical element 434 directs light to one of spectrometer subsystems 461 and 481. In one embodiment, optical element 434 may be a flip mirror. If the flip mirror is in the position shown in FIG. 4, the flip mirror will direct the light into spectrometer subsystem 481. If the flip mirror is flipped out of the position shown in FIG. 4, light goes into spectrometer subsystem 461. In another embodiment, optical element 434 is a dichroic beam splitter.

Spectrometer subsystem 461 covers wavelengths of deep UV to near IR. Spectrometer subsystem 461 is shown to include one or more optical elements 446 and 450 with reflective power, grating 448, filter 452 and detector 454. Optical element 446 directs the light to grating 448, which disperses the light into a spectrum. Light from the grating is directed by optical element 446 to optical element 450, which directs the light through filter 452 to detector 454. Detector 454 generates output responsive to light reflected off the one or more structures on wafer 420. Detector 454 may be a charge coupled device (CCD) or photodiode array (PDA).

Spectrometer subsystem 481 covers wavelengths of IR. Spectrometer subsystem 481 is shown to include one or more optical elements 436 and 440 with reflective power, grating 438, filter 442, and detector 444. Optical element 436 directs the light to grating 438, which disperses the light into a spectrum. Light from the grating is directed by optical element 436 to optical element 440, which directs the light through filter 442 to detector 444. Detector 444 generates output responsive to light reflected off the one or more structures on wafer 420. Detector 444 may be a PDA.

Spectrometer subsystems 461 and 481 may include any type and arrangement of optical elements known in the art of spectroscopic ellipsometry, reflectometry and scatterometry. In one embodiment, the detection subsystem includes first spectrometer subsystem 481 configured to detect the IR light and not the UV light from the one or more structures and second spectrometer subsystem 461 configured to detect the UV light and not the IR light from the one or more structures. For example, the second spectrometer subsystem may be configured to detect deep UV to near IR light and not the IR light from the one or more structures. In this manner, the detection subsystem may include two spectrometers, one dedicated for IR and another dedicated for UV. For example, as shown in FIG. 4, first spectrometer subsystem 481 may be made up of optical elements 436 and 440, grating 438, optical filter 442, and detector 444. These elements may make up an IR spectrometer of the detection subsystem. Second spectrometer subsystem 461 may be made up of optical elements 446 and 450, grating 448, optical filter 452, and detector 454. These elements may make up a UV spectrometer of the system.

The system configurations described herein are compatible with different versions of optical metrology systems. For example, in one embodiment, the illumination and detection subsystems are configured for ellipsometry. The ellipsometry may include any suitable ellipsometry known in the art. For example, the ellipsometry may be spectroscopic ellipsometry (SE). SE can, in general, be Mueller Matrix SE (MMSE) with a single or dual rotating compensator configuration, multiple angle of incidence (AOI) SE, or SE with multiple azimuth angle measurements.

In another embodiment, the illumination and detection subsystems are configured for reflectometry. The reflectometry may include any reflectometry known in the art. In some embodiments, at least one of the illumination and detection subsystems includes an apodizing element, and the illumination and detection subsystems are configured for SE, spectroscopic reflectometry (SR), beam profile ellipsometry (BPE), or beam profile reflectometry (BPR). Apodizing element(s) are preferably located near aperture stops 408 and/or 424. In addition, the embodiments described herein may be configured to include a combination of different subsystems such as SE with SR or SE with angle-resolved reflectometry.

The embodiments described herein also advantageously provide relatively small spot size measurement capability. For example, the embodiments described herein provide a methodology for measuring structures that are characterized by relatively large, micro-scale dimensions (such as HAR structures) with optical metrology in a relatively small area, e.g., an area that is less than 50 microns×50 microns. In one embodiment, the illumination subsystem is configured to direct the light to a spot on the one or more structures, and the spot has at least one lateral dimension that is less than 50 microns. In one such example, if the spot is a circular spot, the circular spot may have a diameter that is less than 50 microns. In another such example, if the spot is an elliptical spot, the minor dimension of the elliptical spot may be less than 50 microns.

Relatively small spot size measurement capability is enabled by using a reflective optics design, such as that described further above, in the case of SE and by using an apodized optics design, such as that described further above, in the case of SE, SR, BPE, or BPR. The systems described herein may be further configured for SE as described in U.S. Pat. No. 5,608,526 to Piwonka-Corle et al. issued on Mar. 4, 1997, which is incorporated by reference as if fully set forth herein. As described in U.S. Pat. No. 5,859,424 to Norton et al. issued on Jan. 12, 1999, which is incorporated by reference as if fully set forth herein, apodizing elements have been used to reduce the spot size in optical measurements. However, it is believed that apodizing elements have not previously been used with IR wavelengths and LSPs.

The system also includes a computer subsystem configured to determine one or more characteristics of the one or more structures using the output. For example, the system shown in FIG. 4 may include a computer subsystem such as computer system 604 shown in FIG. 6, which is described further herein. For example, the computer system shown in FIG. 6 may be coupled to detectors 444 and 454 shown in FIG. 4 by one or more transmission media (not shown), which may include "wired" and/or "wireless" transmission media, such that the computer system can receive the output produced by the detectors. The computer subsystem may be configured to determine any one or more characteristics described herein of any of the one or more structures described herein using the output with any suitable method and/or algorithm known in the art.

In one embodiment, the illumination subsystem is configured to direct different wavelengths of the UV light, visible light, and IR light to the one or more structures sequentially, and the illumination subsystem is configured to change a size and a location of a spot to which the light is directed as the wavelength of the light directed to the one or more structures changes. For example, the embodiments described herein enable a substantially consistent and continuous change of the spot size and spot location as wavelengths are changed across the wide analysis range, from UV to IR. As metrology targets become more complex, changes in wafer characteristics (e.g., CD, line width, thickness, angles, and the like) due to changes in the SE data of metrology targets become increasingly highly correlated and difficult to decouple. However, the extended and substantially continuous wavelength range of the metrology systems described herein aids in breaking correlations of wafer characteristics. The illumination subsystem may direct the different wavelengths of light to the structure(s) in any suitable manner, and the illumination subsystem may be configured to change the size and location of the spot in any suitable manner.

As described above, the detection subsystem may include two spectrometers, one configured for IR light and not UV light and the other for UV light and not IR light. In one such embodiment, wavelength ranges of the first and second spectrometers overlap, and the computer subsystem is configured to combine the output from the first and second spectrometers using the output generated in the wavelength ranges that overlap. For example, the IR and UV spectrometers may overlap in the visible wavelength range, and the output of the IR and UV spectrometers may be stitched together and conditioned for optimizing hardware-to-hardware and tool-to-tool matching and facilitating recipe transfer and hardware adoption. Furthermore, optical designs described herein allow for the use of two or more spectrometers to cover the entire wavelength range and allow stitching of data of different wavelength ranges into one substantially continuous dataset. One key component that allows achieving this in the embodiments described herein is an optical filter described below.

Figure 5:
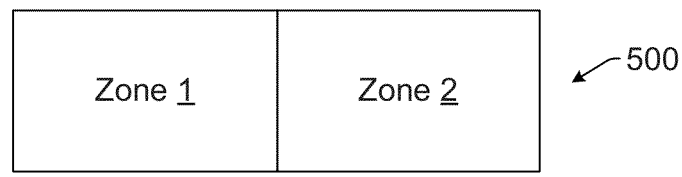
FIG. 5 is a schematic diagram illustrating a plan view of one embodiment of an optical filter that may be included in the system embodiments described herein.

For example, in one embodiment, the illumination subsystem includes an optical filter having a first zone and a second zone on a single substrate. The first zone is configured to be used while the UV light is being directed to the one or more structures by the illumination subsystem, and the second zone is configured to be used while the IR light is being directed to the one or more structures by the illumination subsystem. Therefore, the optical filter may have more than one zone on a single substrate. For example, as shown in FIG. 5, optical filter 500 may include zone 1 and zone 2 formed on a single substrate. The multi-zone filter may be used as optical filter 402 shown in FIG. 4. At least one of the zones may be optimized for UVSE (i.e., SE with shorter wavelengths) and at least one zone may be optimized for IRSE (i.e., SE with longer wavelengths). The UVSE filter zone could be a neutral density (ND) filter for UV light level control or a short pass filter for blocking unwanted IR light from contaminating measurements. The IRSE filter zone could be an ND filter for IR light level control or a long pass filter for blocking unwanted UV light from causing damage to one or more structures formed on the wafer such as resist targets. One or more zones on the filter could also or alternatively be a notch filter for blocking a pump source of an LSP used as the light source. An advantage of the filter embodiments described herein over filters formed on multiple substrates is that there will be the same wedge error across the substrate of the filters described herein, which will minimize changes in the illumination spot position (spot size) on the measurement target of the wafer.

The embodiments described herein are also compatible with metrology approaches such as multiple tool and multiple target analysis including data feed forward or data feed sideways methodology or simultaneous multiple tool and target analysis. Multiple tool and multiple target analysis may be performed as described in U.S. Pat. No. 7,478,019 to Zangooie et al. issued on Jan. 13, 2009, which is incorporated by reference as if fully set forth herein. The use of extended wavelength range can also enhance the concepts of metrology target design as described in U.S. patent application Ser. No. 13/665,436 filed Oct. 31, 2012 by Yoo et al., which published as U.S. Patent Application Publication No. 2013/ on 2013, which is incorporated by reference as if fully set forth herein. Yet other ways to enhance analysis with the extended wavelength range can include principal component analysis (PCA) and other robust statistics methods.

In one embodiment, the one or more structures are not device structures, and the one or more structures include one or more layers included in the device structures having a different thickness than the one or more layers in the device structures. For example, the embodiments described herein can improve the signal-to-noise ratio of the metrology by target design. In particular, the target design may be altered to adjust the thicknesses of the performance-limiting layers (e.g., one or more hard masks) to enhance metrology sensitivity. Therefore, the embodiments described herein may improve signal-to-noise ratio by separate or simultaneous expansion of metrology hardware (via expanded wavelength range) or target design space.

The embodiments described herein can provide significant advantages for a number of different applications. For example, the longer IR wavelengths described herein can be beneficial for implant monitoring applications. The advantage of IR is due to the fact that the concentration of free carriers strongly affects the optical properties of silicon. Similarly, IR wavelength metrology is useful for structures with materials having optical properties that are IR wavelength sensitive. Such structures include some nanowires structures, quantum dots, etc.

In one embodiment, the one or more structures include a material that is opaque to at least some of the light, and the one or more characteristics include a bandgap of the material determined based on a wavelength at which the material becomes opaque and a composition of the material determined based on the bandgap. For example, materials such as gallium arsenide (GaAs), indium phosphate (InP), silicon germanium (SiGe), and others are finding increasing use in semiconductor manufacturing. Since their bandgaps make these materials opaque at shorter wavelengths, extended wavelength range made available by IR is very beneficial. At longer wavelengths these materials become transparent (e.g., GaAs is transparent for wavelengths above 870 nm which corresponds to a 1.42 eV GaAs bandgap), which significantly changes the measured signal thereby boosting sensitivity. Moreover, tracking the offset wavelength when these materials become transparent would allow for composition measurements as the change of composition shifts the bandgap such as Ga composition in indium gallium arsenide (InGaAs) (see, for example, "Band gap versus composition and demonstration of Vegard's law for In1−xGaxAsyP1−y lattice matched to InP," Appl. Phys. Lett. 33 (1978) p. 659).

In another embodiment, the one or more structures include a material that is opaque to at least some of the light, and the one or more characteristics include a bandgap of the material determined based on a wavelength at which the material becomes opaque and a dimension of the one or more structures determined based on the bandgap. For example, the transparency offset may be tracked because it may be directly correlated to geometrical parameters of materials. For example, the diameter of silicon nanowires determines the bandgap (see, for example, "Electronic band structure of high-index silicon nanowires," Phys. Stat. Sol. (b) 242, No. 12, 2474-2479, 2005). Hence, measuring the transparency offset of silicon nanowires would allow for finding their diameters. For this, near-IR wavelengths above 1100 nm are required.

In some metrology use cases, the use of short UV wavelengths can change the properties of the measured structure (e.g., photoresist). Extending the wavelength range as described herein can be beneficial in such use cases.

The use of IR wavelengths as described herein can often allow simplifying the computational part of CD and film metrology. For example, effective medium approximations, in which multiple layers can be replaced by a single effective layer or fewer number of effective layers, can be used when the detailed properties of individual layers are not of critical importance and relatively large scale properties are of more importance.

In one embodiment, the at least one large lateral dimension structure is not one of multiple periodic structures formed on the wafer. In another embodiment, the one or more structures have a period that is greater than 0.5 microns. For example, in some use cases, metrology targets have periods (pitches) that can be large, e.g., on the order of one or several microns. A known limitation of ellipsometry and reflectometry is the potential presence of additional diffracted orders that can contaminate the primary zeroth order signal and degrade the quality of the measurement. However, relatively long wavelengths can provide suppression of high diffraction orders for structures with relatively large pitch. Therefore, in one embodiment, the computer subsystem is configured to not use the output responsive to the UV and visible light to determine the one or more characteristics of the at least one large lateral dimension structure. In this manner, even if the UV and visible light from the structure is detected, output responsive to that light may be ignored during some metrology calculations. As described herein, however, extending the wavelength range to include IR (and essentially doubling the range) allows measuring larger features, e.g., larger pitch targets, etc., which may be particularly useful for SRAM in-cell flash memory characterization.

In another embodiment, the computer subsystem is configured to use the output responsive to the IR light from the one or more structures to determine one or more characteristics of a bottom portion of the at least one HAR structure and to use the output responsive to the visible and UV light from the one or more structures to determine one or more characteristics of a top portion of the at least one HAR structure. The bottom portion of the structure may be defined as a portion of the structure extending from the lowermost surface of the structure and to which the UV and/or visible light cannot penetrate. The top portion of the structure may be defined as a portion of the structure extending from the uppermost surface of the structure and the portion of the structure to which UV and/or visible light can penetrate. For example, the combined use of IR and UV to visible wavelengths (UV-VIS) can simplify the modeling and measurement of complex structures. In particular, a certain subset of the device features, constrained to the top part of the device, may be measured by UV-VIS. Other device features, located in the bottom part of the device, may be measured using IR wavelengths.

In another embodiment, the one or more structures include one or more first structures formed on a first layer on the wafer and one or more second structures formed on a second layer of the wafer below the first layer, and the one or more characteristics include overlay of the one or more first structures with respect to the one or more second structures. For example, the use of IR wavelengths can provide a performance advantage in overlay metrology, especially in devices that use polysilicon or another material that is absorbing in the UV and visible regions, but is transparent at longer wavelengths. The IR permits higher sensitivity to underlying layers and patterns and thereby can significantly increase sensitivity to the relative overlay of the upper device patterns. The computer subsystem may determine the overlay in any suitable manner.

Each of the system embodiments described above may be configured to perform any step(s) of any method(s) described herein. In addition, each of the system embodiments described herein may be configured according to any other embodiments or systems described herein.

Another embodiment relates to a method for determining one or more characteristics of one or more structures formed on a wafer. The method includes directing light to the one or more structures formed on the wafer, which may be performed according to any of the embodiments described herein. The light includes UV light, visible light, and IR light. The one or more structures include at least one HAR structure or at least one large lateral dimension structure. The light and the structure(s) may be further configured as described herein.

The method also includes generating output responsive to light from the one or more structures due to the light directed to the one or more structures, which may be performed according to any of the embodiments described herein. In addition, the method includes determining one or more characteristics of the one or more structures using the output, which may be performed according to any of the embodiments described herein.

Each of the embodiments of the method described above may include any other step(s) of any other method(s) described herein. In addition, each of the embodiments of the method described above may be performed by any of the systems described herein.

Figure 6:
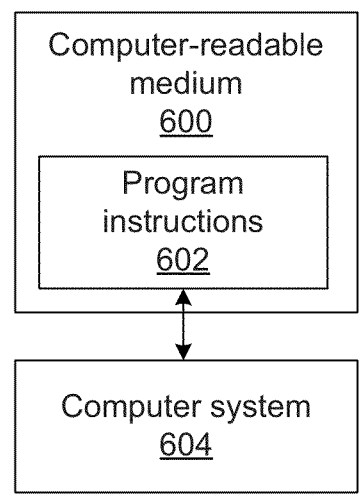
FIG. 6 is a block diagram illustrating one embodiment of a non-transitory computer-readable medium.

Another embodiment relates to a non-transitory computer-readable medium containing program instructions stored therein for causing a computer system to perform a computer-implemented method for determining one or more characteristics of one or more structures formed on a wafer. One embodiment of such a computer-readable medium is shown in FIG. 6. In particular, computer-readable medium 600 contains program instructions 602 stored therein for causing computer system 604 to perform a computer-implemented method for determining one or more characteristics of one or more structures formed on a wafer.

The computer-implemented method includes any step(s) described above with respect to the computer subsystem of the system. For example, the computer-implemented method may include determining one or more characteristics of the one or more structures using output that is responsive to light from the one or more structures due to the light directed to the one or more structures. The computer-implemented method may also include any other step(s) of any other method(s) described herein. In addition, the computer-readable medium may be further configured as described herein.

Program instructions 602 implementing methods such as those described herein may be stored on computer-readable medium 600. The computer-readable medium may be a non-transitory computer-readable storage medium such as a magnetic or optical disk, a magnetic tape, or any other suitable non-transitory computer-readable medium known in the art.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), or other technologies or methodologies, as desired.

Computer system 604 may take various forms, including a personal computer system, mainframe computer system, workstation, image computer, parallel processor, or any other device known in the art. In general, the term "computer system" may be broadly defined to encompass any device having one or more processors, which executes instructions from a memory medium.

Further modifications and alternative embodiments of various aspects of the invention will be apparent to those skilled in the art in view of this description. For example, metrology systems and methods for high aspect ratio and large lateral dimension structures are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to determine one or more characteristics of one or more structures formed on a wafer, comprising:
   an illumination subsystem configured to direct light to the one or more structures formed on the wafer, wherein the light comprises ultraviolet light, visible light, and infrared light, and wherein the one or more structures comprise at least one high aspect ratio structure or at least one large lateral dimension structure;
   a detection subsystem configured to generate output responsive to light from the one or more structures due to the light directed to the one or more structures; and
   a computer subsystem configured to determine one or more characteristics of the one or more structures using the output, wherein the computer subsystem is further configured to use the output responsive to the infrared light from the one or more structures to determine one or more characteristics of a bottom portion of the at least one high aspect ratio structure and to use the output responsive to the visible and ultraviolet light from the one or more structures to determine one or more characteristics of a too portion of the at least one high aspect ratio structure.

2. The system of claim 1, wherein the at least one high aspect ratio structure comprises alternating layers of different materials having different optical properties.

3. The system of claim 1, wherein the at least one large lateral dimension structure is not one of multiple periodic structures formed on the wafer.

4. The system of claim 1, wherein the one or more structures have a period that is greater than 0.5 microns.

5. The system of claim 1, wherein the illumination subsystem comprises at least one laser sustained plasma light source.

6. The system of claim 1, wherein the illumination subsystem is further configured to direct the light to a spot on the one or more structures, and wherein the spot has at least one lateral dimension that is less than 50 microns.

7. The system of claim 1, wherein the illumination subsystem is further configured to direct different wavelengths of the ultraviolet light, visible light, and infrared light to the one or more structures sequentially, and wherein the illumination subsystem is further configured to change a size and a location of a spot to which the light is directed as the wavelength of the light directed to the one or more structures changes.

8. The system of claim 1, wherein the illumination subsystem comprises an optical filter having a first zone and a second zone on a single substrate, wherein the first zone is configured to be used while the ultraviolet light is being directed to the one or more structures by the illumination subsystem, and wherein the second zone is configured to be used while the infrared light is being directed to the one or more structures by the illumination subsystem.

9. The system of claim 1, wherein the illumination and detection subsystems are further configured for ellipsometry.

10. The system of claim 1, wherein the illumination and detection subsystems are further configured for spectroscopic ellipsometry.

11. The system of claim 1, wherein the illumination and detection subsystems are further configured for reflectometry.

12. The system of claim 1, wherein at least one of the illumination and detection subsystems includes an apodizing element, and wherein the illumination and detection subsystems are further configured for spectroscopic ellipsometry, spectroscopic reflectometry, beam profile ellipsometry, or beam profile reflectometry.

13. The system of claim 1, wherein the detection subsystem comprises a first spectrometer subsystem configured to detect the infrared light and not the ultraviolet light from the one or more structures and a second spectrometer subsystem configured to detect the ultraviolet light and not the infrared light from the one or more structures, wherein wavelength ranges of the first and second spectrometers overlap, and wherein the computer subsystem is further configured to combine the output from the first and second spectrometers using the output generated in the wavelength ranges that overlap.

14. The system of claim 1, wherein the computer subsystem is further configured to not use the output responsive to the ultraviolet and visible light to determine the one or more characteristics of the at least one large lateral dimension structure.

15. The system of claim 1, wherein the one or more structures are not device structures, and wherein the one or more structures comprise one or more layers included in the device structures having a different thickness than the one or more layers included in the device structures.

16. The system of claim 1, wherein the one or more structures comprise a material that is opaque to at least some of the light, and wherein the one or more characteristics comprise a bandgap of the material determined based on a wavelength at which the material becomes opaque and a composition of the material determined based on the bandgap.

17. The system of claim 1, wherein the one or more structures comprise a material that is opaque to at least some of the light, and wherein the one or more characteristics comprise a bandgap of the material determined based on a wavelength at which the material becomes opaque and a dimension of the one or more structures determined based on the bandgap.

18. The system of claim 1, wherein the one or more structures comprise one or more first structures formed on a first layer on the wafer and one or more second structures formed on a second layer of the wafer below the first layer, and wherein the one or more characteristics comprise overlay of the one or more first structures with respect to the one or more second structures.

19. A method for determining one or more characteristics of one or more structures formed on a wafer, comprising:
 directing light to the one or more structures formed on the wafer, wherein the light comprises ultraviolet light, visible light, and infrared light, and wherein the one or more structures comprise at least one high aspect ratio structure or at least one large lateral dimension structure;
 generating output responsive to light from the one or more structures due to the light directed to the one or more structures; and
 determining one or more characteristics of the one or more structures using the output, wherein determining the one or more characteristics comprises using the output responsive to the infrared light from the one or more structures to determine one or more characteristics of a bottom portion of the at least one high aspect ratio structure and using the output responsive to the visible and ultraviolet light from the one or more structures to determine one or more characteristics of a top portion of the at least one high aspect ratio structure.

* * * * *